US012251326B2

(12) United States Patent
Yamamoto et al.

(10) Patent No.: US 12,251,326 B2
(45) Date of Patent: Mar. 18, 2025

(54) SYNTHETIC RESIN STENT

(71) Applicant: JMS CO., LTD., Hiroshima (JP)

(72) Inventors: Ayaka Yamamoto, Hiroshima (JP);
Shuji Fukutaki, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 762 days.

(21) Appl. No.: 17/599,371

(22) PCT Filed: Mar. 30, 2020

(86) PCT No.: PCT/JP2020/014486
§ 371 (c)(1),
(2) Date: Sep. 28, 2021

(87) PCT Pub. No.: WO2020/196911
PCT Pub. Date: Oct. 1, 2020

(65) Prior Publication Data
US 2022/0183866 A1 Jun. 16, 2022

(30) Foreign Application Priority Data
Mar. 28, 2019 (JP) .................. 2019-063126

(51) Int. Cl.
*A61F 2/90* (2013.01)
(52) U.S. Cl.
CPC ........ *A61F 2/90* (2013.01); *A61F 2210/0004* (2013.01)
(58) Field of Classification Search
CPC .... A61F 2/90; A61F 2/852; A61F 2/86; A61F 2/88; A61F 2/885; A61F 2210/0004; A61F 2250/0028
See application file for complete search history.

(56) References Cited

U.S. PATENT DOCUMENTS 6,241,757 B1    6/2001   An
6,312,458 B1 *  11/2001  Golds .................. A61F 2/88
                                                    623/1.33

(Continued)

FOREIGN PATENT DOCUMENTS

CN    105997298 A    10/2016
JP    H10272190 A    10/1998

(Continued)

*Primary Examiner* — Paul B Prebilic

(74) *Attorney, Agent, or Firm* — Muncy, Geissler, Olds & Lowe, P.C.

(57) ABSTRACT

A stent can ensure storability in thin tubular members such as delivery systems and is insusceptible to positional displacement after placement of the stent in an affected part of a bodily conduit. This synthetic resin comprises a tubular first braid component comprising a plurality of fibers that are braided into a net-like form, and a second braid component comprising a plurality of fibers that are disposed braided into the first braid component to form an annular shape. The first braid component includes a plurality of first fibers, a plurality of second fibers, and a plurality of first intersections. The second braid component includes a plurality of wave-like third fibers disposed separated in an axial direction and a plurality of wave-like fourth fibers disposed separated in the axial direction. At least one of the first intersections is disposed in an intersection region surrounded by the third fiber and the fourth fiber.

5 Claims, 7 Drawing Sheets

(56) References Cited

U.S. PATENT DOCUMENTS

| | | |
|---|---|---|
| 2010/0049302 A1 | 2/2010 | Kang |
| 2013/0245745 A1 | 9/2013 | Vong et al. |
| 2022/0211524 A1* | 7/2022 | Ide .......................... A61F 2/852 |

FOREIGN PATENT DOCUMENTS

| | | |
|---|---|---|
| JP | 2009160079 A | 7/2009 |
| JP | 2010521217 A | 6/2010 |
| JP | 2017047003 A | 3/2017 |
| JP | 2017169990 A | 9/2017 |
| KR | 10-20180003877 A | 1/2018 |
| WO | WO 2017/038145 A1 | 3/2017 |

* cited by examiner

SYNTHETIC RESIN STENT

TECHNICAL FIELD

The present invention relates to a synthetic resin stent such as a biodegradable stent.

BACKGROUND ART

Stenotic diseases (such as tumors and inflammations) in natural tracts such as blood vessels and gastrointestinal tracts are heretofore treated by placing a stent at a stenotic site and dilating the stenotic site. Stents made of metal or synthetic resin are known, for example. Among these, when a metal stent is removed from the body, a surgical intervention is needed and imposes a significant burden on the patient. Therefore, use of a metal stent is limited to cases such as malignant tumors for which semi-permanent placement or surgical procedures are planned. Against such a background, a biodegradable stent as a synthetic resin stent has been proposed as a stent for use in cases where a metal stent cannot be used (see, for example, Patent Document 1).

A synthetic resin stent is inferior to a metal stent, in self-expandability, restorability, adherence to the gastrointestinal tract such as the intestinal tract, and trackability to peristaltic movement of the gastrointestinal tract; therefore, required performance may not be achieved when a synthetic resin stent is manufactured in the same shape as a metal stent.

Patent Document 1: Japanese Unexamined Patent Application, Publication No. 2009-160079

DISCLOSURE OF THE INVENTION

Problems to be Solved by the Invention

Achieving an anchoring effect may be conceivable by forming the ends of the stent into a flare shape, i.e., making the diameter of the ends of the stent larger than the diameter of the central portion. However, even if the ends are formed into a flare shape, a biodegradable stent is inferior in strength to a metal stent; therefore, when pressure is applied to the flare-shaped portion from outside in the radial direction, it is difficult to maintain the shape and sufficiently achieve an anchoring effect.

Enhancing the resistance of the biodegradable stent to pressure from outside in the radial direction may be conceivable by thickening the fiber composing the biodegradable stent. However, when the fiber composing the biodegradable stent is thickened, it becomes difficult to load the stent into a fine tubular member such as a delivery system to be used when the stent is placed at a stenotic site.

Accordingly, it is an object of the present invention to provide a synthetic resin stent that is unlikely to cause migration after placing the stent at an affected site inside a natural tract, while ensuring loadability into a fine tubular member such as a delivery system.

Means for Solving the Problems

The invention relates to a synthetic resin stent, including a first woven component portion being tubular and composed of a plurality of fibers woven into a mesh, and a second woven component portion composed of a plurality of fibers arranged so as to be woven into the first woven component portion and configured into an annular shape; the first woven component portion preferably includes a plurality of first fibers extending so as to be inclined at a predetermined angle with respect to the axial direction, a plurality of second fibers extending so as to intersect with the first fibers, and a plurality of first intersecting points configured with intersections of the plurality of first fibers and the plurality of second fibers; the second woven component portion preferably includes a plurality of wave-shaped third fibers arranged so as to be spaced apart in the axial direction, and a plurality of wave-shaped fourth fibers arranged so as to be spaced apart in the axial direction; and at least one first intersecting point of the plurality of first intersecting points is preferably arranged in intersecting regions surrounded by the third fibers and the fourth fibers.

The plurality of intersecting regions are preferably formed side by side in the circumferential direction of the first woven component portion; and the plurality of first intersecting points are preferably arranged side by side in the circumferential direction of the first woven component portion and arranged in the plurality of intersecting regions, respectively.

In a configuration in which the first intersecting points are arranged in the intersecting regions, respectively, the third fibers are preferably arranged in a state of being hookable by one or more of the first fibers, the second fibers and the fourth fibers, in relation to movement in a direction in which an overlapping portion of the third fibers and the fourth fibers shrinks in size; and the fourth fibers is preferably arranged in a state of being hookable by one or more of the first fibers, the second fibers and the third fibers, in relation to movement in a direction in which the overlapping portion of the third fibers and the fourth fibers shrinks in size.

A plurality of configurations are provided in which the first intersecting point is arranged in the intersecting region, in which the synthetic resin stent is preferably configured to partly include a configuration, in which the third fibers and the fourth fibers are arranged in a state of being mutually hookable, in relation to movement in a direction in which the overlapping portion of the third fibers and the fourth fibers shrinks in size, and arranged in a state of not being hookable by the first fibers and the second fibers when the third fibers and the fourth fibers move.

A loop having a loop shape is preferably formed at the top of the peaks of the wave-shaped third fibers and/or the wave-shaped fourth fibers, the loop arranged so as to surround any one or more of the first fibers, the second fibers, the third fibers and the fourth fibers.

The second woven component portion is preferably formed of synthetic resin fiber having an expansion force higher than the first woven component portion.

The present invention relates to a synthetic resin stent, including a first woven component portion being tubular and composed of one more fibers configured into a mesh, and a second woven component portion arranged so as to be woven into the first woven component portion and composed of one or more fibers configured into an annular shape; the first woven component portion preferably includes a plurality of first fibers repeatedly bent so as to be inclined at a predetermined angle with respect to the axial direction and extending in the axial direction, a plurality of second fibers arranged to include a portion intersecting with the first fibers and repeatedly bent so as to be inclined at a predetermined angle with respect to the axial direction and extending in the axial direction, and a plurality of first intersecting regions configured with intersections of the plurality of first fibers and the plurality of second fibers; the second woven component portion preferably includes a plurality of third fibers repeatedly bent so as to be inclined at a predetermined angle with respect to the axial direction and extending in the circumferential direction, a plurality of fourth fibers arranged to include a portion intersecting with the third fibers and repeatedly bent so as to be inclined at a predetermined angle with respect to the axial direction and extending in the axial direction, and a plurality of second intersecting regions configured with intersections of the plurality of third fibers and the plurality of fourth fibers; and the first intersecting regions and the second intersecting regions are preferably arranged to at least partly overlap with each other.

In a configuration in which the first intersecting region is arranged to overlap with the second intersecting region, the first fibers are preferably arranged in a state of being hookable by one or more of the third fibers and the fourth fibers, in relation to movement in a direction in which an overlapping portion of the first fibers and the second fibers shrinks in size; and the second fibers are preferably arranged in a state of being hookable by one or more of the third fibers and the fourth fibers, in relation to movement in a direction in which an overlapping portion of the first fibers and the second fibers shrinks in size.

Effects of the Invention

The present invention can provide a synthetic resin stent that is unlikely to cause migration after placing the stent at an affected site inside the natural tract, while ensuring loadability into a fine tubular member such as a delivery system.

PREFERRED MODE FOR CARRYING OUT THE INVENTION

Hereinafter, each embodiment of a synthetic resin stent of the present invention will be described with reference to the drawings.

First Embodiment

Figure 1:
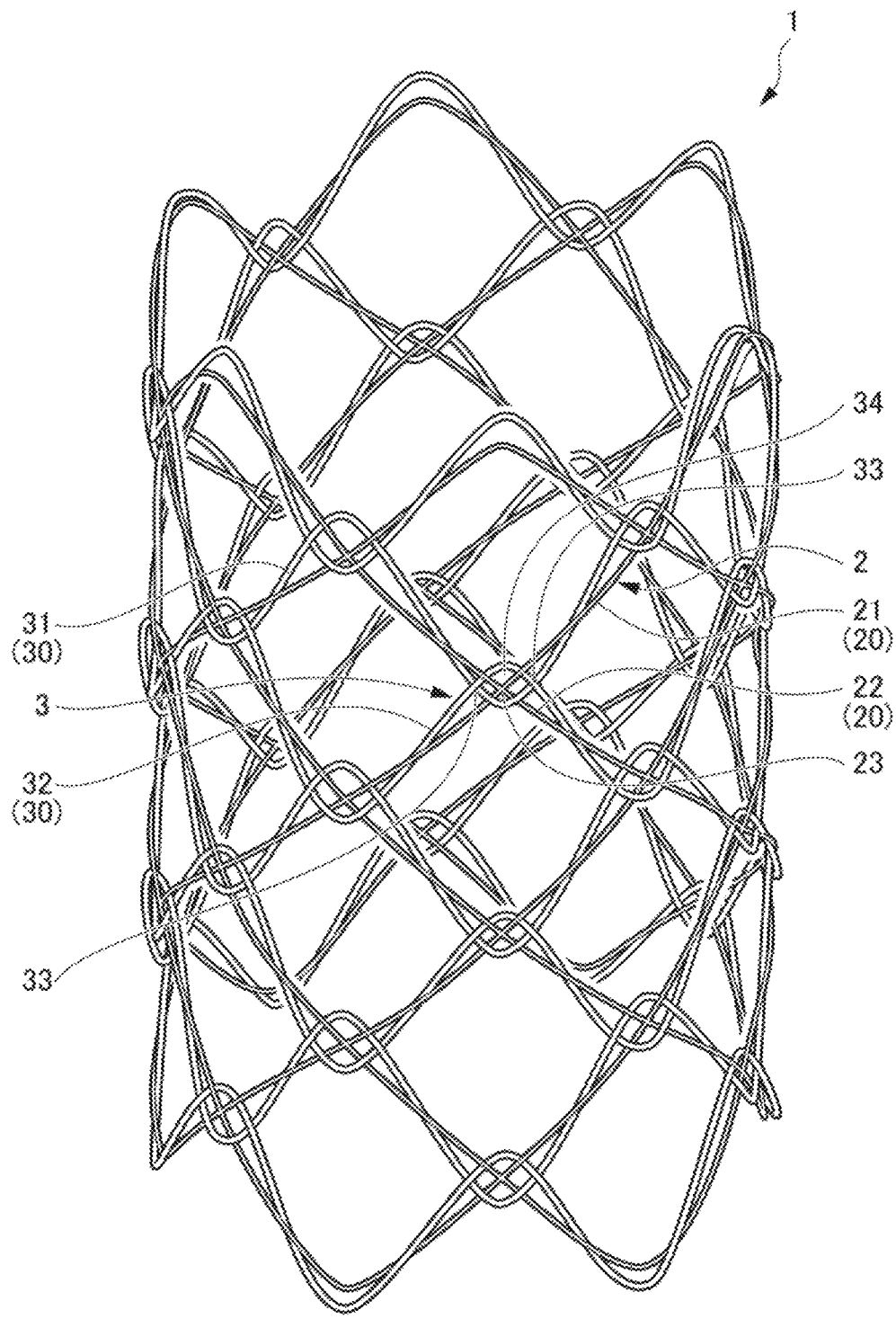
FIG. 1 is a perspective view illustrating a biodegradable stent according to a first embodiment of the present invention.
Figure 2:
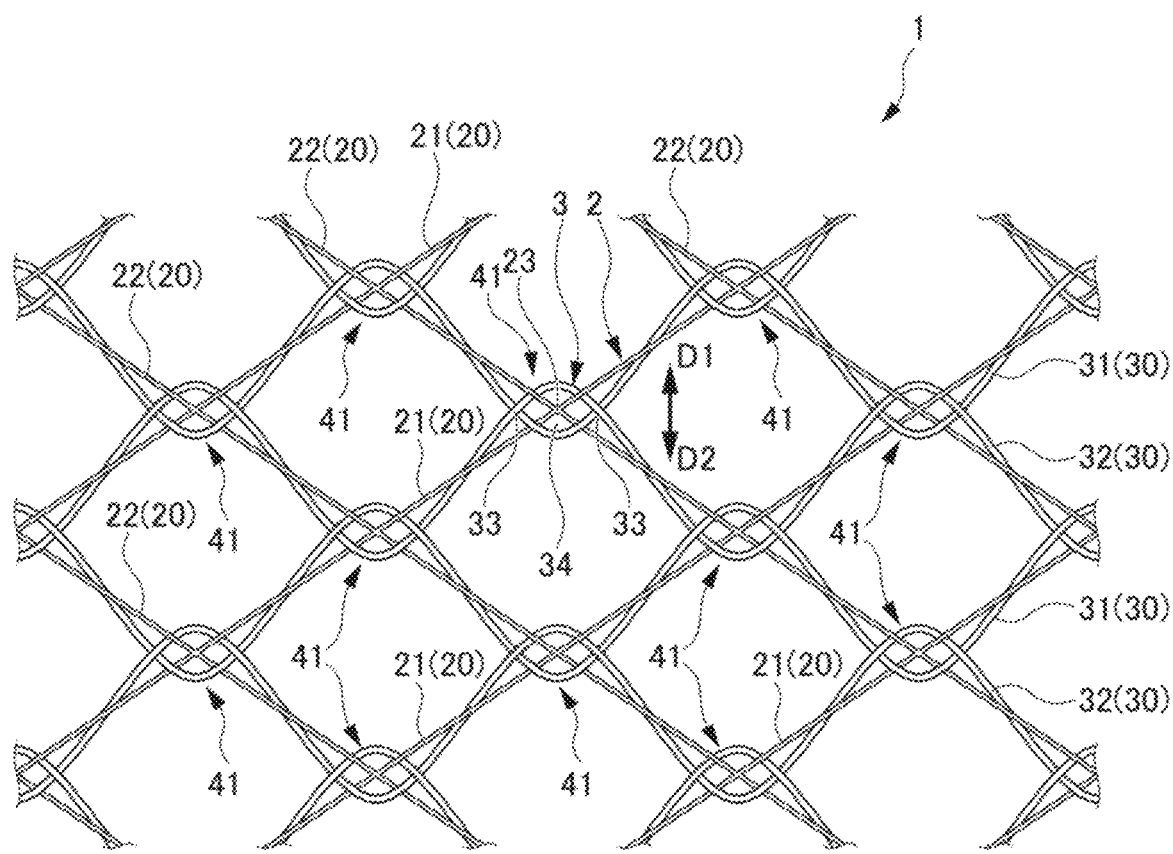
FIG. 2 is an enlarged view of the biodegradable stent illustrated in FIG. 1.

With reference to FIGS. 1 and 2, a biodegradable stent 1 according to the first embodiment will be described. FIG. 1 is a perspective view illustrating the biodegradable stent 1 according to the first embodiment of the present invention. FIG. 2 is an enlarged view of the biodegradable stent 1 illustrated in FIG. 1.

The synthetic resin stent of the present embodiment is the biodegradable stent 1 composed of biodegradable fiber, and includes a meshed tubular portion 2 (first woven component portion) and a wavily woven portion 3 (second woven component portion) arranged so as to be woven in the meshed tubular portion 2, as illustrated in FIGS. 1 and 2.

The meshed tubular portion 2 is woven into a mesh of a plurality of fibers 20 and configured into a tubular structure, and includes a multitude of argyle voids formed of the fibers 20 on the outer periphery and arranged in an orderly fashion. The mesh of the meshed tubular portion 2 becomes sparse in the axial direction when the biodegradable stent 1 is in the reduced diameter state, and becomes dense in the axial direction when the biodegradable stent 1 is in the expanded diameter state.

In the present embodiment, as illustrated in FIG. 2, the plurality of fibers 20 configuring the meshed tubular portion 2 includes a plurality of first fibers 21 and a plurality of second fibers 22. As viewed from the side, the meshed tubular portion 2 includes a multitude of argyle voids formed of the first fibers 21 and the second fibers 22, and includes a plurality of first intersecting points 23 configured by intersections of the plurality of first fibers 21 and the plurality of second fibers 22.

The plurality of first fibers 21 are formed of synthetic resin fiber extending so as to be inclined at a predetermined angle with respect to the axial direction. In the present embodiment, as illustrated in FIG. 2, the plurality of first fibers 21 are arranged so as to be inclined and extending from the upper right side to the lower left side.

The plurality of second fibers 22 are formed of synthetic resin fiber extending so as to intersect with the plurality of first fibers 21. In the present embodiment, as illustrated in FIG. 2, the plurality of second fibers 22 are arranged so as to be inclined and extending from the upper left side to the lower right side.

The material of the first fibers 21 and the second fiber 22 is not limited; however, a material having a high degree of rigidity is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of rigidity. In particular, for example, poly-lactic acid (PLA) or poly-L-lactic acid (PLLA) is preferably used as the material of the fiber configuring the first fibers 21 and the second fiber 22. In the present embodiment, the first fibers 21 and the second fiber 22 are formed from polylactic acid (PLA), for example.

In the case of using biodegradable fiber as the fiber 20, the diameter thereof is preferably 0.1 mm to 0.4 mm. When the diameter of the biodegradable fiber 20 is less than 0.1 mm, the strength of the biodegradable stent 1 tends to decrease. When the diameter of the biodegradable fiber 20 exceeds 0.4 mm, the diameter increases in the reduced diameter state, so that it tends to be difficult to load the biodegradable stent 1 into a fine tubular member such as a delivery system. The upper limit of the diameter of the biodegradable fiber 20 is further preferably 0.3 mm, from a perspective of loading into a delivery system having a small inner diameter. The lower limit of the diameter of the biodegradable fiber 20 is more preferably 0.2 mm, from a perspective of maintaining high strength. In the present embodiment, biodegradable fiber having a diameter of 0.2 mm and biodegradable fiber having a diameter of 0.3 mm are used as the fibers 20.

As illustrated in FIG. 1, the plurality of annularly formed wave-shaped fibers 30 of the wavily woven portion 3 are arranged so as to be woven in the meshed tubular portion 2. In the present embodiment, the plurality of fibers 30 configuring the wavily woven portion 3 include: a plurality of third fibers 31 arranged so as to be spaced apart in the axial direction; and a plurality of fourth fibers 32 arranged so as to be spaced apart in the axial direction. The wavily woven portion 3 includes a plurality of second intersecting points 33 formed by intersections of the plurality of third fibers 31 and the plurality of fourth fibers 32.

As illustrated in FIG. 2, the third fibers 31 and the fourth fibers 32 are formed into a wave shape extending in the circumferential direction of the meshed tubular portion 2, in which peaks and valleys consecutively alternate. The third fibers 31 and the fourth fibers 32 are arranged such that the mutual convex portions face each other and the facing convex portions partly overlap with each other.

More specifically, the third fibers 31 and the fourth fibers 32 are formed into a wave shape having peaks convex toward the first direction D1 side and peaks convex toward the second direction D2 side, in which mutual peaks partly overlap with each other and intersect at two second intersecting points 33, as viewed from the side. The wavily woven portion 3 includes an intersecting region 34 as viewed from the side. The intersecting region 34 is a region surrounded by the third fiber 31 and the fourth fiber 32 between the two adjacent second intersecting points 33 among the plurality of second intersecting points 33, where the mutual convex portions of the third fiber 31 and the fourth fiber 32 overlap with each other. The plurality of intersecting regions 34 are formed side by side in the circumferential direction of the meshed tubular portion 2 being tubular.

The material of the synthetic resin fiber configuring the third fiber 31 and the fourth fiber 32 is not limited in particular; however, a material having a high degree of restorability is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of restorability. For example, polydioxanone (PDO) is preferably used as the material of the third fiber 31 and the fourth fiber 32.

In the case of using biodegradable fiber as the fiber 30, the diameter thereof is preferably 0.1 mm to 0.4 mm. In the present embodiment, the biodegradable fiber having a diameter of 0.15 mm to 0.22 mm is used as the fiber 30.

The first intersecting points 23 of the meshed tubular portion 2 are arranged in the plurality of intersecting regions 34 of the wavily woven portion 3, respectively, as the meshed tubular portion 2 is viewed from the side. The plurality of first intersecting points 23 are arranged in the plurality of intersecting regions 34, respectively, and arranged side by side in the circumferential direction of the meshed tubular portion 2 being tubular. The portion where the first intersecting point 23 of the meshed tubular portion 2 is arranged in the intersecting region 34 of the wavily woven portion 3 configures a first hooking portion 41. The biodegradable stent 1 of the present embodiment includes the plurality of first hooking portions 41, in which a row of the plurality of first hooking portions 41 arranged side by side in the circumferential direction is formed throughout the axial direction.

In the first hooking portion 41, the third fiber 31 is arranged in the state of being hookable by one or more of the first fibers 21, the second fibers 22, and the fourth fibers 32, in relation to movement in a direction in which the mutually overlapping convex portion of the third fiber 31 and the fourth fiber 32 shrinks in size. The fourth fiber 32 is arranged in the state of being hookable by one or more of the first fibers 21, the second fibers 22, and the third fibers 31, in relation to movement in a direction in which the mutually overlapping convex portion of the third fiber 31 and the fourth fiber 32 shrinks in size.

In the present embodiment, the third fiber 31 and the fourth fiber 32 configuring the wavily woven portion 3 are formed of synthetic resin fiber having an expansion force higher than the first fibers 21 and the second fiber 22 configuring the meshed tubular portion 2; therefore, the bent portion thereof has a property of returning to a straight line. At least part of the third fiber 31 and the fourth fiber 32 is arranged so as to be woven in the meshed tubular portion 2, can apply a force to increase the diameter of the biodegradable stent 1, and can deform the meshed tubular portion 2 from the reduced diameter state to the expanded diameter state.

The configuration of the first hooking portion 41 will be described. FIG. 2 is a view, in which the radial direction of the tubular biodegradable stent 1 in FIG. 1 is rearranged along the direction perpendicular to the paper (direction penetrating the paper) of FIG. 2. Therefore, the inside of the biodegradable stent 1 in the radial direction is the backside in the vertical direction of the paper of FIG. 2; and the outer side of the biodegradable stent 1 in the radial direction is the frontside in the vertical direction of the paper of FIG. 2.

As illustrated in FIG. 2, the first fibers 21 and the second fibers 22 of the meshed tubular portion 2 decussate at the first intersecting point 23 in the first hooking portion 41.

The third fiber 31 is arranged on the frontside or backside in FIG. 2 with respect to the fourth fiber 32 (outer side or inner side of the biodegradable stent 1 in the radial direction) at both of the two second intersecting points 33. As a result, the third fiber 31 and the fourth fiber 32 of the biodegradable stent 1 are arranged in the state of not being mutually hookable, in relation to mutual movement toward the first direction D1 or the second direction D2.

The first intersecting point 23 of the first fiber 21 and the second fiber 22 is arranged in the intersecting region 34 surrounded by the third fiber 31 and the fourth fiber 32, in the overlapping convex portion between the third fiber 31 and the fourth fiber 32 of the wavily woven portion 3.

As illustrated in FIG. 2, the first fiber 21 is arranged so as to be inclined and extending from the upper right side to the lower left side in the intersecting region 34. From the upper right side toward the lower left side, the first fiber 21 passes the frontside of one of the third fiber 31 and the fourth fiber 32, intersects with the second fiber 22 at the first intersecting point 23, and passes the backside of the other one of the third fiber 31 and the fourth fiber 32. As illustrated in FIG. 2, the second fiber 22 is arranged so as to be inclined and extending from the upper left side to the lower right side in the intersecting region 34. The second fiber 22 passes the frontside of one of the third fiber 31 and the fourth fiber 32, intersects with the first fiber 21 at the first intersecting point 23, and passes the backside of the other one of the third fiber 31 and the fourth fiber 32.

The first fiber 21, the second fiber 22, the third fiber 31, and the fourth fiber 32 are arranged as described above, whereby, in the first hooking portion 41, one of the third fiber 31 and the fourth fiber 32 having a peak convex toward the first direction D1 is arranged in the state of being hookable by the first fiber 21 and the second fiber 22, in relation to movement in a direction in which the mutually overlapping convex portion of the third fiber 31 and the fourth fiber 32 shrinks in size; and the other one of the third fiber 31 and the fourth fiber 32 having a peak convex toward the second direction D2 opposite to the first direction D1 is arranged in the state of being hookable by the first fiber 21 and the second fiber 22, in relation to movement in a direction in which the mutually overlapping convex portion of the third fiber 31 and the fourth fiber 32 shrinks in size.

The biodegradable stent 1 as described above may be manufactured by weaving the wavily woven portion 3 and then weaving the meshed tubular portion 2, or conversely, by weaving the meshed tubular portion 2 and then weaving the wavily woven portion 3. In the case of manufacturing the biodegradable stent 1, for example, a tubular tool with a plurality of pins standing on a circumferential surface at a predetermined interval may be used, the fiber is hooked by the plurality of pins to weave the wavily woven portion 3, and then the fiber of the meshed tubular portion 2 passes through the intersecting region of the wavily woven portion 3, whereby the biodegradable stent 1 can be manufactured.

The meshed tubular portion 2 of the biodegradable stent 1 configured as described above is woven into a tubular structure with the first fiber 21 and the second fiber 22 inclined with respect to the axial direction, whereby the shape of the stent is maintained in the tubular structure. The wave-shaped wavily woven portion 3 is woven into the meshed tubular portion 2, and the wavily woven portion 3 (third fiber 31 and fourth fiber 32) is formed of synthetic resin fiber having an expansion force higher than the meshed tubular portion 2 (first fiber 21 and second fiber 22), and the bent portion thereof has a property of returning to a straight line. Therefore, the wavily woven portion 3 is woven into a wave shape so as to circle the meshed tubular portion 2 in the circumferential direction, whereby the wavily woven portion 3 can apply a force to increase the diameter of the biodegradable stent 1, and can enhance the expansion force. Thus, the expansion force of the biodegradable stent 1 in the radial direction can be strengthened to achieve self-expandability. Adherence to the wall of the gastrointestinal tract can be increased, and trackability to gastrointestinal motility can be achieved.

According to the biodegradable stent 1 of the first embodiment described above, the following effects can be achieved.

(1) The biodegradable stent 1 is configured to include the meshed tubular portion 2 being tubular and composed of the plurality of fibers 21 and 22 woven into a mesh, and the wavily woven portion 3 composed of the plurality of fibers 31 and 32 annularly formed and woven into the meshed tubular portion 2; the meshed tubular portion 2 is configured to include the plurality of first fibers 21 extending so as to be inclined at a predetermined angle with respect to the axial direction, the plurality of second fibers 22 extending so as to intersect with the first fibers 21, and the plurality of first intersecting points 23 formed at intersections of the plurality of first fibers 21 and the plurality of second fibers 22; the wavily woven portion 3 is configured to include the plurality of wave-shaped third fibers 31 arranged so as to be spaced apart in the axial direction, and the plurality of wave-shaped fourth fibers 32 arranged so as to be spaced apart in the axial direction; and the at least one of the first intersecting points 23 is arranged in the intersecting region 34 surrounded by the third fibers 31 and the fourth fibers 32.

As a result, the meshed tubular portion 2 of the biodegradable stent 1 is woven into a tubular structure with the first fibers 21 and the second fibers 22 inclined with respect to the axial direction, whereby the shape of the stent is maintained in the tubular structure. The wave-shaped wavily woven portion 3 is woven into the meshed tubular portion 2, and the first intersecting point 23 of the meshed tubular portion 2 is arranged in the intersecting region 34 of the wavily woven portion 3, whereby the wavily woven portion 3 can apply a force to increase the diameter and can enhance the expansion force in the radial direction. Thus, the expansion force of the biodegradable stent 1 in the radial direction can be strengthened to achieve self-expandability. Adherence to the wall of the gastrointestinal tract can be increased, and trackability to gastrointestinal motility can be achieved. Therefore, the stent can ensure loadability into a fine tubular member such as a delivery system, in which migration of the stent is unlikely to occur after placement at the affected site of the natural tracts.

(2) The plurality of intersecting regions 34 are formed side by side in the circumferential direction of the meshed tubular portion 2 being tubular; and the plurality of first intersecting points 23 are formed side by side in the circumferential direction of the meshed tubular portion 2 being tubular, and arranged in the plurality of intersecting regions 34, respectively. As a result, the wavily woven portion 3 can be woven along the circumferential direction, whereby the expansion force of the biodegradable stent 1 in the radial direction can be further strengthened.

(3) When the first intersecting point 23 of the meshed tubular portion 2 is configured so as to be arranged in the intersecting region 34 of the wavily woven portion 3, the third fiber 31 is arranged in the state of being hookable by one or more of the first fiber 21, the second fiber 22, and the fourth fiber 32, in relation to movement in a direction in which the overlapping portion of the third fiber 31 and the fourth fiber 32 shrinks in size; and the fourth fiber 32 is arranged in the state of being hookable by one or more of the first fiber 21, the second fiber 22, and the third fiber 31, in relation to movement in a direction in which the overlapping portion of the third fiber 31 and the fourth fiber 32 shrinks in size. As a result, any of these fibers is hooked by the third fiber 31 and the fourth fiber 32 of the wavily woven portion 3, whereby displacement of the first intersecting point 23 can be prevented.

(4) The wavily woven portion 3 (third fiber 31 and fourth fiber 32) is formed of synthetic resin fiber having an expansion force higher than the meshed tubular portion 2 (first fiber 21 and second fiber 22). As a result, the meshed tubular portion 2 being tubular is formed of the first fiber 21 and the second fiber 22, and the third fiber 31 and fourth fiber 32 can expand the first fiber 21 and the second fiber 22 in the radial direction; therefore, the expansion force in the radial direction can be further enhanced.

Second Embodiment

Figure 3:
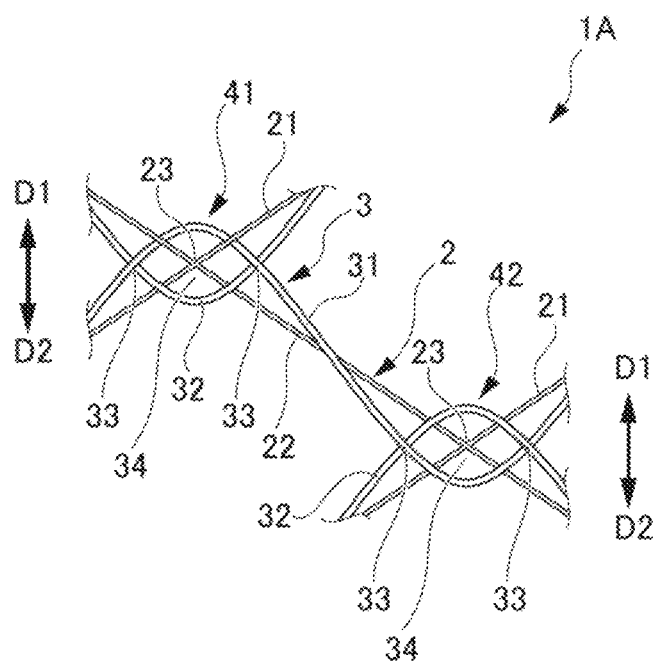
FIG. 3 is a view illustrating a biodegradable stent according to a second embodiment.

A biodegradable stent 1A of a second embodiment will be described. FIG. 3 is a view illustrating the biodegradable stent 1A according to the second embodiment. As illustrated in FIG. 3, the biodegradable stent 1A of the second embodiment is configured to include a first hooking portion 41 (left side in FIG. 3) and a second hooking portion 42 (right side in FIG. 3). The plurality of first hooking portions 41 and the plurality of second hooking portions 42 are spirally and alternately arranged in the circumferential direction in the biodegradable stent 1A.

Since the configuration of the first hooking portion 41 illustrated in FIG. 3 is similar to that of the first hooking portion 41 described in the first embodiment, description thereof is omitted.

The configuration of the second hooking portion 42 will be described. As illustrated in FIG. 3, the first fiber 21 and the second fiber 22 of the meshed tubular portion 2 decussate at the first intersecting point 23 in the second hooking portion 42 as well, similar to the first hooking portion 41 of the first embodiment.

In the second hooking portion 42, the third fiber 31 is arranged frontside of the fourth fiber 32 at one of the two second intersecting points 33 (left side in FIG. 3) and arranged backside of the fourth fiber 32 at the other one of the second intersecting points 33 (right side in FIG. 3). As a result, the third fiber 31 and the fourth fiber 32 are arranged in the state of being mutually hookable, in relation to movement in a direction in which the mutually overlapping convex portion of the third fiber 31 and the fourth fiber 32 shrinks in size.

The first intersecting point 23 of the first fiber 21 and the second fiber 22 is arranged in the intersecting region 34 surrounded by the third fiber 31 and the fourth fiber 32 of the wavily woven portion 3.

As illustrated in FIG. 3, the first fiber 21 is arranged so as to be inclined and extending from the upper right side to the lower left side in the intersecting region 34, and passes the backside of the fourth fiber 32, intersects with the second fiber 22 at the first intersecting point 23, and passes the backside of the third fiber 31, from the upper right side to the lower left side. As illustrated in FIG. 3, the second fiber 22 is arranged so as to be inclined and extending from the upper left side to the lower right side in the intersecting region 34, passes the backside of the fourth fiber 32, intersects with the first fiber 21 at the first intersecting point 23, and passes the backside of the third fiber 31, from the upper left side to the lower right side. In other words, in the second hooking portion 42, the first fiber 21 and the second fiber 22 in their entirety are arranged backside of the third fiber 31 and the fourth fiber 32, whereby the third fiber 31 and the fourth fiber 32 in their entirety are arranged frontside of the first fiber 21 and the second fiber 22.

The first fiber 21, the second fiber 22, the third fiber 31, and the fourth fiber 32 are arranged as above, whereby, in the second hooking portion 42, the third fiber 31 and the fourth fiber 32 are arranged in the state of being mutually hookable, in relation to movement in a direction in which the mutually overlapping convex portion of the third fiber 31 and the fourth fiber 32 shrinks in size; the third fiber 31 and the fourth fiber 32 in their entirety are arranged frontside of the first fiber 21 and the second fiber 22; and the third fiber 31 and the fourth fiber 32 are arranged in the state of not being hookable by the first fiber 21 and the second fiber 22, in relation to movement of the third fiber 31 and the fourth fiber 32 in the first direction D1 or the second direction D2 direction.

According to the biodegradable stent 1A of the second embodiment described above, in addition to the effects (1) to (4) described above, the following effects can be achieved.

(5) The plurality of configurations are provided, in which the first intersecting point 23 of the meshed tubular portion 2 is arranged in the intersecting region 34 of the wavily woven portion 3; and the third fiber 31 and fourth fiber 32 are arranged in the state of being mutually hookable, in relation to movement in a direction in which the overlapping portion of the third fiber 31 and fourth fiber 32 shrinks in size, and also arranged in the state of not being hookable by the first fiber 21 and the second fiber 22 when the third fiber 31 and fourth fiber 32 move. As a result, the third fiber 31 and/or the fourth fiber 32 are/is arranged in the state of not being hookable by the first fiber 21 and the second fiber 22, whereby the length in the axial direction is unlikely to be restricted when the biodegradable stent 1A is extended; therefore, loadability into a delivery system can be improved.

Third Embodiment

Figure 4:
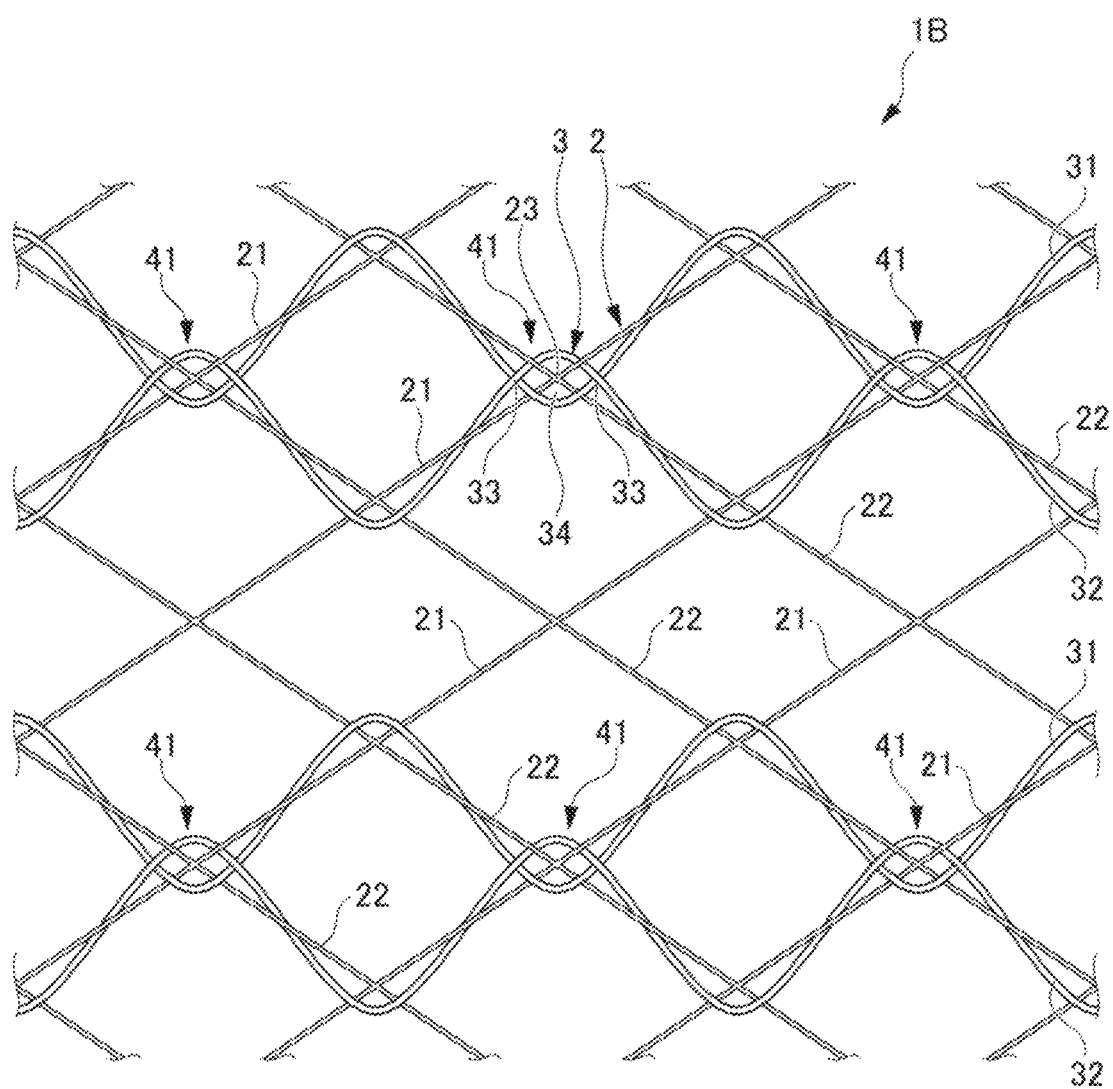
FIG. 4 is a view illustrating a biodegradable stent according to a third embodiment.

A biodegradable stent 1B of a third will be described. FIG. 4 is a view illustrating the biodegradable stent 1B according to the third embodiment. As compared with the biodegradable stent 1 of the first embodiment, in the case of the biodegradable stent 1B of the third embodiment, the rows of the plurality of first hooking portions 41 arranged in the circumferential direction are arranged so as to be spaced one row apart from each other, instead of being packed in the axial direction of the biodegradable stent 1A, in the wave-shaped wavily woven portion 3 (second woven component portion) woven into the meshed tubular portion 2 (first woven component portion).

As illustrated in FIG. 4, the wavily woven portion 3 is configured to include a row in which the plurality of first hooking portion 41 are arranged side by side in the circumferential direction, and a row without the first hooking portions 41, in the axial direction of the meshed tubular portion 2 having the plurality of first intersecting points 23. The first intersecting point 23 is arranged in the intersecting region 34 of the wavily woven portion 3 in the first hooking portion 41, in the row in which the plurality of first hooking portions 41 are arranged side by side in the circumferential direction. The plurality of first intersecting points 23 are arranged side by side in the circumferential direction, in the row without the first hooking portions 41.

According to the biodegradable stent 1B of the third embodiment described above, in addition to the effects (1) to (5) described above, the following effects can be achieved.

(6) The rows of the plurality of first hooking portions 41 arranged in the circumferential direction are arranged so as to be spaced one row apart from each other in the axial direction. As a result, the rows without the first hooking portions 41 are provided, instead of packing the first hooking portions 41 in the axial direction of the biodegradable stent 1B, whereby the length in the axial direction is unlikely to be restricted by the third fiber 31 and the fourth fiber 32 when the biodegradable stent 1B is extended; therefore, loadability into a delivery system can be improved.

Fourth Embodiment

Figure 5:
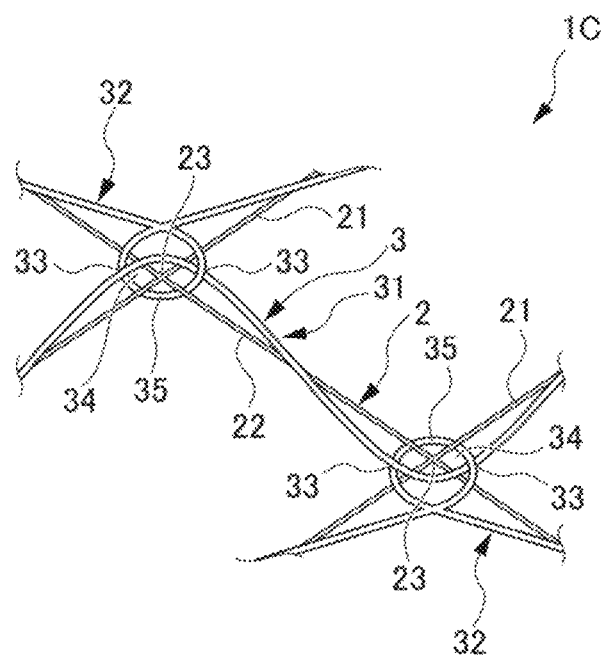
FIG. 5 is a view illustrating a biodegradable stent according to a fourth embodiment.

A biodegradable stent 1C of a fourth embodiment will be described. FIG. 5 is a view illustrating the biodegradable stent 1C according to the fourth embodiment.

As illustrated in FIG. 5, the biodegradable stent 1C of the fourth embodiment includes a plurality of loops 35 formed at the top of the peaks of the wave-shaped fourth fiber 32. The loop 35 is formed into a loop shape surrounding the first fiber 21, the second fiber 22, the third fiber 31, and the fourth fiber 32, in which the first intersecting point 23 of the meshed tubular portion 2 is arranged in the intersecting region 34 of the wavily woven portion 3.

The plurality of loops 35 may be consecutively provided at the top of the peaks of the wave-shaped fourth fiber 32, or may be intermittently provided at the top of the plurality of peaks of the wave-shaped fourth fiber 32. The loops 35 may not be configured to surround all of the first fiber 21, the second fiber 22, the third fiber 31, and the fourth fiber 32, or may be configured to surround only part of the first fiber 21, the second fiber 22, the third fiber 31, and the fourth fiber 32.

According to the biodegradable stent 1C of the fourth embodiment described above, in addition to the effects (1) to (6) described above, the following effects can be achieved.

(7) The loops 35 are provided at the top of the peaks of the wave-shaped third fiber 31 and/or the wave-shaped fourth fiber 32. Here, for example, in the case without the loops 35 at the top of the peaks of the wavily woven portion 3, only an expansion force in the radial direction is applied to the wave-shaped third fiber 31 and the wave-shaped fourth fiber 32 of the wavily woven portion 3; therefore, it is difficult to control the diametrical size of the biodegradable stent 1C. In contrast, in the present invention, the loops 35 can apply a contraction force in the radial direction; therefore, the diametrical size of the biodegradable stent 1C can be controlled.

Fifth Embodiment

Figure 6:
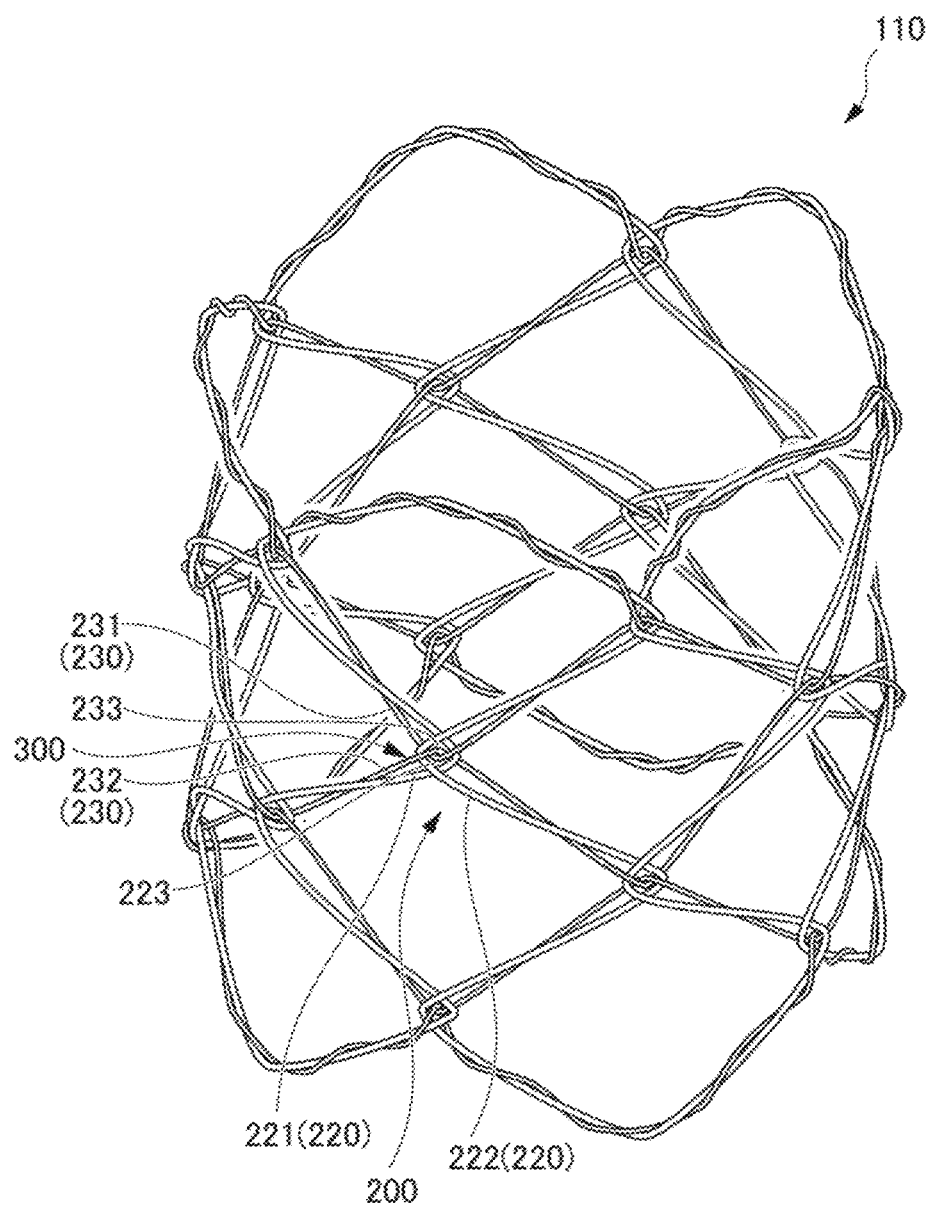
FIG. 6 is a perspective view illustrating the biodegradable stent according to the second embodiment of the present invention.
Figure 7:
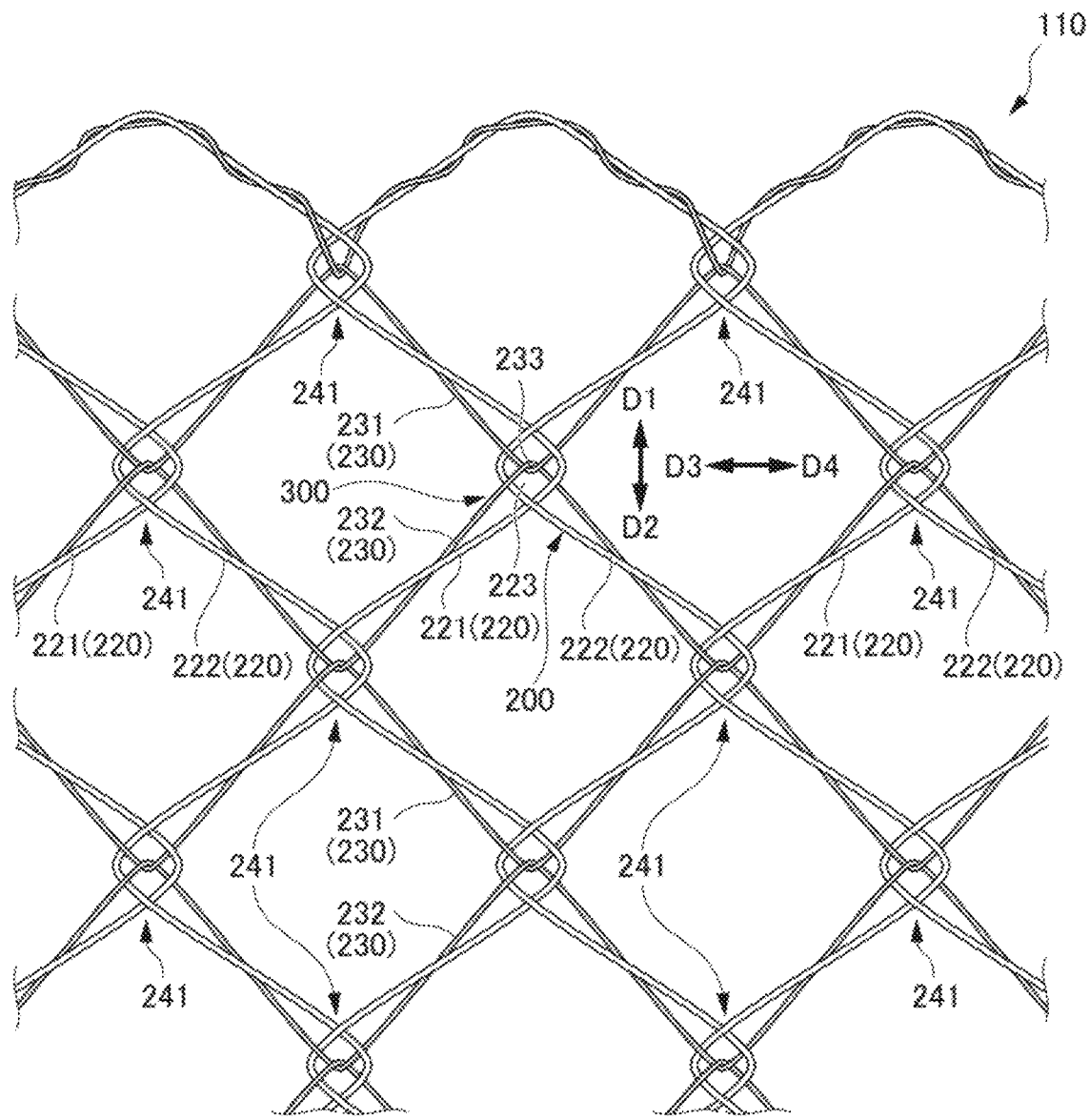
FIG. 7 is an enlarged view of the biodegradable stent illustrated in FIG. 6.

Referring to FIGS. 6 and 7, a biodegradable stent 110 according to fifth embodiment will be described. FIG. 6 is a perspective view illustrating the biodegradable stent 110 according to the fifth embodiment of the present invention. FIG. 7 is an enlarged view of the biodegradable stent 110 illustrated in FIG. 6. In the biodegradable stent 110 illustrated in FIG. 7, one side in the axial direction is referred to as a first direction D1, and the other side in the axial direction is referred to as a second direction D2. In the biodegradable stent 110, one side in the circumferential direction is referred to as a third direction D3 (left side of FIG. 7), and the other side in the circumferential direction is referred to as a fourth direction D4 (right side of FIG. 7).

As illustrated in FIGS. 6 and 7, the synthetic resin stent of the present embodiment is the biodegradable stent 110 composed of biodegradable fiber, and includes a first bent woven portion 200 (first woven component portion) and a second bent woven portion 300 (second woven component portion) arranged so as to be woven in the first bent woven portion 200.

The first bent woven portion 200 is formed into a mesh, in which a plurality of fibers 220 repeatedly bent so as to extend in the axial direction are arranged in the circumferential direction and formed into a tubular structure. In the present embodiment, as illustrated in FIG. 7, the fiber 220 configuring the first bent woven portion 200 is configured with a plurality of first fibers 221 and a plurality of second fibers 222.

The plurality of first fibers 221 are formed of synthetic resin fiber repeatedly bent so as to be inclined at a predetermined angle with respect to the axial direction and extending in the axial direction. The plurality of first fibers 221 are repeatedly bent and extend in the axial direction so as to shuttle in a predetermined range of width in the circumferential direction of the first bent woven portion 200.

The plurality of second fibers 222 are arranged to include a portion intersecting with the plurality of first fibers 221, and formed of synthetic resin fiber repeatedly bent so as to shuttle and extending in the axial direction. The plurality of second fibers 222 are repeatedly bent and extend in the axial direction so as to shuttle in a predetermined range of width in the circumferential direction of the first bent woven portion 200.

In the present embodiment, the plurality of first fibers 221 and the plurality of second fibers 222 are composed of a single fiber, folding back at the upper and lower ends of the first bent woven portion 200 in the axial direction. The plurality of first fibers 221 and the plurality of second fibers 222 are part of a single fiber. In other words, the first fiber 221 and the second fiber 222 are alternately arranged in the circumferential direction of the first bent woven portion 200. The first bent woven portion 200 may be configured with a plurality of fibers.

More specifically, as illustrated in FIG. 7, the first fiber 221 and the second fiber 222 both include a plurality of bent portions including peaks convex toward the third direction D3 side and peaks convex toward the fourth direction D4 side. As viewed from the side, the first fiber 221 and the second fiber 222 are arranged to have bent portions overlapping with each other and intersect in the first intersecting region 223. The first fiber 221 and the second fiber 222 are formed such that the region surrounded by the first fiber 221 and the second fiber 222 is an opening having a substantially diamond shape in the first intersecting region 223.

In the first intersecting region 223, the first fiber 221 and the second fiber 222 may be arranged so as to overlap with each other as viewed from the side, and may be hooked by each other or may not be hooked by each other. In the present embodiment, the bent portions of the first fiber 221 and the second fiber 222 are hooked by each other in the upper end portion and the lower end portion of the biodegradable stent 110 in the axial direction, and are not hooked by each other in portions excluding the upper end portion and the lower end portion of the biodegradable stent 110 in the axial direction. The first intersecting regions 223 are arranged side by side in both the axial direction and the circumferential direction of the first bent woven portion 200.

The first intersecting region 223 is formed such that the region surrounded by the first fiber 221 and the second fiber 222 is an opening. However, the size of the opening of the first intersecting region 223 is not limited. In the first intersecting region 223, the first fiber 221 and the second fiber 222 may pull each other in the overlapping portion in a direction to shrink in size, so that the first fiber 221 and the second fiber 222 may be hooked by each other, whereby the region surrounded by the first 221 and the second fiber 222 may not be an opening.

The material of the first fiber 221 and the second fiber 222 is not limited in particular; however, a material having a high degree of rigidity is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of rigidity. In particular, for example, polylactic acid (PLA) or poly-L-lactic acid (PLLA) is preferably used as the material of the fiber composing the first fiber 221 and the second fiber 222. In the present embodiment, the first fibers 221 and the second fiber 222 are formed from polylactic acid (PLA), for example.

In the case of using biodegradable fiber as the fiber 220, the diameter thereof is preferably 0.1 mm to 0.4 mm. When the diameter of the biodegradable fiber 220 is less than 0.1 mm, the strength of the biodegradable stent 110 tends to decrease. When the diameter of the biodegradable fiber 20 exceeds 0.4 mm, the diameter in the reduced diameter state increases, so that it tends to be difficult to load the biodegradable stent 110 into a fine tubular member such as a delivery system. The upper limit of the diameter of the biodegradable fiber 20 is further preferably 0.3 mm, from a perspective of loading into a delivery system having a small inner diameter. The lower limit of the diameter of the biodegradable fiber 220 is more preferably 0.2 mm, from a perspective of maintaining high strength. In the present embodiment, biodegradable fiber having a diameter of 0.2 mm and biodegradable fiber having a diameter of 0.3 mm are used as the fibers 220.

As illustrated in FIGS. 6 and 7, the second bent woven portion 300 is arranged so as to be woven into the first bent woven portion 200, in which a plurality of circularly configured fibers 230 repeatedly bent so as to extend in the circumferential direction are arranged side by side in the axial direction. In the present embodiment, as illustrated in FIG. 7, the fiber 230 configuring the second bent woven portion 300 is configured with a plurality of third fibers 231 and a plurality of fourth fibers 232.

The plurality of third fibers 231 are formed of synthetic resin fiber repeatedly bent so as to be inclined at a predetermined angle with respect to the axial direction and extending in the circumferential direction. The plurality of third fibers 231 are repeatedly bent and extend in the circumferential direction so as to shuttle in a predetermined range of width in the axial direction of the second bent woven portion 300.

The plurality of fourth fibers 232 are arranged to include a portion intersecting with the plurality of third fibers 231, and formed of synthetic resin fiber repeatedly bent so as to extend in the circumferential direction. The plurality of fourth fibers 232 are repeatedly bent and extend in the circumferential direction so as to shuttle in a predetermined range of width in the axial direction of the second bent woven portion 300.

More specifically, the third fiber 231 and the fourth fiber 232 both include a plurality of bent portions including peaks convex toward the first direction D1 side and peaks convex toward the second direction D2 side. As viewed from the side, the third fiber 231 and the fourth fiber 232 are arranged to have bent portions overlapping with each other and intersect in the second intersecting region 233. In the second intersecting region 233, the third fiber 231 and the fourth fiber 232 may be arranged so as to overlap with each other as viewed from the side, and may be hooked by each other or may not be hooked by each other. In the present embodiment, the bent portions of the third fiber 231 and the fourth fiber 232 are hooked by each other in the second intersecting region 233, and the region surrounded by the third fiber 231 and the fourth fiber 232 is not an opening. The second intersecting regions 233 are arranged side by side in the axial direction and the circumferential direction of the second bent woven portion 300.

The bent portions of the third fiber 231 and the fourth fiber 232 are hooked by each other, and the region surrounded by the third 231 and the fourth fiber 232 is not an opening in the second intersecting region 233, which is not limited, however. The region surrounded by the third 231 and the fourth fiber 232 may be an opening in the second intersecting region 233, and the size of the opening in the second intersecting region 233 is not limited.

Of the plurality of third fibers 231 and the plurality of fourth fibers 232, the third fiber 231 or the fourth fiber 232 arranged at the upper end or the lower end of the biodegradable stent 110 is arranged so as to be wound around the first fiber 221 or the second fiber 222 of the first bent woven portion 200.

The material of the synthetic resin fiber configuring the third fiber 231 and the fourth fiber 232 is not limited in particular; however, a material having a high degree of restorability is preferable. Examples of the biodegradable resin may include homopolymer, copolymer, or blend polymer composed of L-lactic acid, D-lactic acid, DL-lactic acid, glycolic acid, ε-caprolactone, or para-dioxanone. Non-biodegradable resin may also be used as long as the material has a high degree of restorability. For example, polydioxanone (PDO) is preferably used as the material of the third fiber 231 and the fourth fiber 232.

In the case of using biodegradable fiber as the fiber 230, the diameter thereof is preferably 0.1 mm to 0.4 mm. In the present embodiment, the biodegradable fiber having a diameter of 0.15 mm to 0.22 mm is used as the fiber 230.

The first intersecting region 223 of the first bent woven portion 200 and the second intersecting region 233 of the second bent woven portion 300 are arranged so as to be at least partially overlapping with each other, as the biodegradable stent 110 is viewed from the side. The at least partially overlapping portion of the second intersecting region 233 of the second bent woven portion 300 and the second intersecting region 233 of the first bent woven portion 200 configures a hooking portion 241. The biodegradable stent 110 of the present embodiment includes a plurality of hooking portions 241, in which a row of the hooking portions 241 arranged in the circumferential direction is formed throughout the axial direction.

The configuration of the hooking portion 241 will be described. FIG. 7 is a view, in which the radial direction of the tubular biodegradable stent 110 in FIG. 6 is rearranged along the direction perpendicular to the paper (direction penetrating the paper) of FIG. 7. Therefore, the inside of the biodegradable stent 110 in the radial direction is the backside in the vertical direction of the paper of FIG. 7; and the outer side of the biodegradable stent 110 in the radial direction is the frontside in the vertical direction of the paper of FIG. 7. Some parts of the upper and lower ends of the biodegradable stent 110 in the axial direction are woven to prevent the fibers from coming apart. Here, the hooking portion 241 in the present embodiment will be described for the portions excluding the upper and lower ends of the biodegradable stent 110 in the axial direction.

As illustrated in FIG. 7, the second intersecting region 233 of the third fiber 231 and the fourth fiber 232 is arranged in the first intersecting region 223 surrounded by the first fiber 221 and the second fiber 222, in the hooking portion 241.

The first fiber 221 and the second fiber 222 of the first bent woven portion 200 are arranged to include an opening in the first intersecting region 223 in the hooking portion 241, in which a bent portion convex toward the third-direction D3 side and a bent portion convex toward the fourth-direction D4 side overlap with each other.

The third fiber 231 and the fourth fiber 232 of the second bent woven portion 300 are arranged in the state in which a bent portion convex toward the first direction D1 side and a bent portion convex toward the second direction D2 side are hooked by each other, in the second intersecting region 233 in the hooking portion 241.

As illustrated in FIG. 7, the bent portion convex toward the third direction D3 side in the first fiber 221 and the second fiber 222 of the first bent woven portion 200 passes the backside of the third fiber 231 and the fourth fiber 232 on the apex side of the convex portion (third direction D3 side), and passes the frontside of the third fiber 231 and the fourth fiber 232 on the opening side of the convex portion (fourth direction D4 side), in the hooking portion 241. The bent portion convex toward the fourth direction D4 side in the first fiber 221 and the second fiber 222 passes the frontside of the third fiber 231 and the fourth fiber 232 on the apex side of the convex portion (fourth direction D4 side), and passes the frontside of the third fiber 231 and the fourth fiber 232 on the opening side of the convex portion (third direction D3 side). The bent portion convex toward the third direction D3 side in the first fiber 221 and the second fiber 222 passes the frontside of the bent portion convex toward the fourth direction D4 side.

The first fiber 221, the second fiber 222, the third fiber 231, and the fourth fiber 232 are arranged as above, whereby, in the hooking portion 241, the first fiber 221 is arranged in the state of being hookable by the third fiber 231 and the fourth fiber 232, in relation to movement in a direction in which the mutually overlapping convex portion of the first fiber 221 and the second fiber 222 shrinks in size; and the second fiber 222 is arranged in the state of being hookable by the third fiber 231 and the fourth fiber 232, in relation to movement in a direction in which the mutually overlapping convex portion of the first fiber 221 and the second fiber 222 shrinks in size.

The biodegradable stent 110 as described above may be manufactured by forming the second bent woven portion 300 and then forming the first bent woven portion 200, or conversely, by forming the first bent woven portion 200 and then forming the second bent woven portion 300.

The biodegradable stent 110 configured as described above is formed into a tubular structure with the first fiber 221 and the second fiber 222 repeatedly bent so as to be inclined with respect to the axial direction and extending in the axial direction in the first bent woven portion 200, whereby the shape of the stent is maintained in the tubular structure. The second bent woven portion 300 is woven into the first bent woven portion 200, the second bent woven portion 300 (third fiber 231 and fourth fiber 232) is formed of synthetic resin fiber having a higher expansion force than the first bent woven portion 200 (first fiber 221 and second fiber 222), and the bent portion thereof has a property of returning to a straight line. Therefore, the second bent woven portion 300 is woven and repeatedly bent so as to circle the first bent woven portion 200 in the circumferential direction, whereby the second 300 can apply a force to increase the diameter of the biodegradable stent 110, and can enhance the expansion force. Thus, the expansion force of the biodegradable stent 110 in the radial direction can be strengthened to achieve self-expandability. Adherence to the wall of the gastrointestinal tract can be increased, and trackability to gastrointestinal motility can be achieved.

According to the biodegradable stent 110 of the fifth embodiment described above, the following effects can be achieved.

(8) The biodegradable stent 110 is configured to include the tubular first bent woven portion 200 composed of one or more fibers formed into a mesh, and the second bent woven portion 300 composed of one or more fibers annularly arranged so as to be woven into the first bent woven portion 200; the first bent woven portion 200 is configured to include the plurality of first fibers 221 repeatedly bent so as to be inclined at a predetermined angle with respect to the axial direction and extending in the axial direction, the plurality of second fiber 222 repeatedly bent so as to be inclined at a predetermined angle with respect to the axial direction and extending in the axial direction and arranged to include a portion intersecting with the first fiber 221, and the plurality of first intersecting regions 223 configured by intersections of the plurality of first fibers 221 and the plurality of second fibers 222; the second bent woven portion 300 is configured to include the plurality of third fibers 231 repeatedly bent so as to be inclined at a predetermined angle with respect to the axial direction and extending in the circumferential direction; the plurality of fourth fiber 232 repeatedly bent so as to be inclined at a predetermined angle with respect to the axial direction and extending in the axial direction and arranged to include a portion intersecting with the third fiber 231, and the plurality of second intersecting regions 233 configured by intersections of the plurality of third fibers 231 and the plurality of fourth fibers 232; and the first intersecting region 223 and the second intersecting region 233 are arranged so as to be at least partially overlapping with each other.

As a result, the first fiber 221 and the second fiber 222 repeatedly bent so as to be inclined at a predetermined angle with respect to the axial direction and extending in the axial direction maintains the first bent woven portion 200 in the tubular structure, whereby the tubular structure of the biodegradable stent 110 is maintained. The second bent woven portion 300 is woven into the first bent woven portion 200, and the first intersecting region 223 of the first bent woven portion 200 and the second intersecting region 233 of the second bent woven portion 300 are arranged to at least partially overlap with each other, whereby the second bent woven portion 300 can apply a force to increase the diameter, and can enhance the expansion force in the radial direction. Thus, the expansion force of the biodegradable stent 110 in the radial direction can be strengthened to achieve self-expandability. Adherence to the wall of the gastrointestinal tract can be increased, and trackability to gastrointestinal motility can be achieved. Therefore, the stent can ensure loadability into a fine tubular member such as a delivery system, in which migration of the stent is unlikely to occur after placement at the affected site of the natural tracts.

(9) In the configuration in which the first intersecting region 223 of the first bent woven portion 200 and the second intersecting region 233 of the second bent woven portion 300 are arranged to overlap each other, the first fiber 221 is arranged in the state of being hookable by one or more of the third fiber 231 and the fourth fiber 232, in relation to movement in a direction in which the overlapping portion of the first fiber 221 and the second fiber 222 shrinks in size; and the second fiber 222 is arranged in the state of being hookable by one or more of the third fiber 231 and the fourth fiber 232, in relation to movement in a direction in which the overlapping portion of the first fiber 221 and the second fiber 222 shrinks in size. As a result, the first fiber 221 and the second fiber 222 of the first bent woven portion 200 are hooked by any one of the third fiber 231 and the fourth fiber 232, whereby displacement of the first intersecting region 223 and the second intersecting region 233 can be prevented.

A manufacture example and an example of the biodegradable stent of the first to fourth embodiments will be briefly described. In the present manufacture example, the biodegradable stent 1A of the second embodiment (see FIG. 3) and the biodegradable stent 1B of the third embodiment (see FIG. 4) are manufactured by braiding six PLA fibers (three fibers having a fiber diameter of 0.2 mm, and three fibers having a fiber diameter of 0.3 mm), and using PDO fiber having a fiber diameter of 0.15 mm to 0.22 mm to manufacture a wave shape. The biodegradable stent 1C of the fourth embodiment (see FIG. 5) is manufactured by braiding six PLA fibers (having a diameter of 0.2 mm) and using PDO fiber to manufacture a wave shape with a fiber diameter of 0.30 mm to 0.349 mm, and a loop shape with a fiber diameter of 0.15 mm to 0.22 mm. The biodegradable stents 1A, 1B and 1C are formed by weaving and winding the PLA fiber around the PDO fiber having a wave shape, whereby the shape of the stents is unlikely to collapse.

The biodegradable stents 1A, 1B and 1C are manufactured under the conditions described above, whereby a stent loadable into a delivery system for the small intestine ($\varphi$2.8 mm) can be achieved. In the case of use in other gastrointestinal tracts, the diameter of the delivery system increases and the fiber diameter can increase as well, whereby a stent having further higher strength can be expected to be manufactured. The fiber diameter as well as the stent diameter and length may be arbitrary.

The biodegradable stents 1A and 1C thus prepared were used to conduct the following experiment. A tool manufactured in-house to simulate peristaltic movement was used to conduct a migration test on the stents. The tool for use in the present test simulates peristaltic movement, in which the stent was placed inside a tube mimicking the intestinal tract, and the tube was squeezed 10 times with a tool having a hole-diameter of 10 mm, assuming that the intestinal tract shrinks to φ10 mm due to peristaltic movement.

In an intestinal tract model in which the diameter of the intestinal tract expands to φ17 mm and shrinks to φ10 mm during peristaltic movement, the biodegradable stent 1A of the second embodiment (stent having a length of 55 mm) moved by 35 mm. In an intestinal tract model in which the diameter of the intestinal tract expands to φ12 mm and shrinks to φ10 mm during peristaltic movement, the biodegradable stent 1C of the fourth embodiment (stent having a length of 36 mm) moved by 10 mm. In the same intestinal tract models, a metallic stent (stent having a length of 110 mm) moved by 40 mm, suggesting that the biodegradable stents 1A and 1C of the second and fourth embodiments, respectively, have trackability to the intestinal tract.

The preferred embodiments of the synthetic resin stent of the present invention have been described above; however, the present invention is not limited to the embodiments and can be modified as appropriate.

For example, the biodegradable stent composed of biodegradable fiber has been used as a synthetic resin stent in the embodiments, which are not limited. In other words, nonbiodegradable synthetic resin fiber may be used to compose a stent.

The plurality of first hooking portions 41 are provided to the biodegradable stent 1 in its entirety, in the first embodiment. The first hooking portions 41 and the second hooking portions 42 are alternately provided, in the second embodiment. The plurality of first hooking portions 41 are arranged side by side in the circumferential direction, in the third embodiment. However, the present invention is not limited to the embodiments, and the first hooking portions 41 and/or the second hooking portions 42 may not be provided to the biodegradable stent in its entirety, or may be provided to part of the biodegradable stent.

In the embodiments described above, the loop 35 is provided at the top of the peaks of the wave-shaped fourth fiber 32, which is not limited, and may be provided at the top of the peaks at the wave-shaped third fiber 31.

EXPLANATION OF REFERENCE NUMERALS 1, 1A, 1B, 1C, 110: biodegradable stent (synthetic resin stent)
2: meshed tubular portion (first woven component portion)
3: wavily woven portion (second woven component portion)
21: first fiber
22: second fiber
23: first intersecting point
31: third fiber
32: fourth fiber
33: second intersecting point
34: intersecting region
35: loop
200 first bent woven portion (first woven component portion)
300: second bent woven portion (second woven component portion)
221: first fiber
222: second fiber
223: first intersecting region
231: third fiber
232: fourth fiber
233: second intersecting region
241: hooking portion

The invention claimed is:

1. A synthetic resin stent, comprising:
a first woven component portion being tubular and composed of a plurality of fibers woven into a mesh; and a second woven component portion composed of a plurality of fibers arranged so as to be woven into the first woven component portion and configured into an annular shape, wherein
the first woven component portion includes a plurality of first fibers extending so as to be inclined at a predetermined angle with respect to an axial direction, a plurality of second fibers extending so as to intersect with the first fibers, and a plurality of first intersecting points configured with intersections of the plurality of first fibers and the plurality of second fibers,
the second woven component portion includes a plurality of wave-shaped third fibers arranged so as to be spaced apart in the axial direction, and a plurality of wave-shaped fourth fibers arranged so as to be spaced apart in the axial direction, and
the third fibers and the fourth fibers are arranged alternately in the axial direction,
the third fibers and the fourth fibers are each formed into a wave shape having peaks convex toward a first direction side and peaks convex toward a second direction side which is opposite to the first direction,
the peaks convex toward the first direction side of at least one of the third fibers partly overlap the peaks convex toward the second direction side of the fourth fibers adjacent to the third fibers in the first direction and are arranged to intersect with the fourth fibers at two second intersecting points, and the peaks convex toward the second direction side of at least one of the third fibers partly overlap the peaks convex toward the first direction side of the fourth fibers adjacent to the third fibers in the second direction and are arranged to intersect with the fourth fibers at the two second intersecting points,
at least one first intersecting point of the plurality of first intersecting points is arranged in intersecting regions surrounded by the third fibers and the fourth fibers between the two second intersecting points at a portion where the peaks of the third fibers and the fourth fibers overlap with each other.

2. The synthetic resin stent according to claim 1, wherein
the plurality of intersecting regions are formed side by side in a circumferential direction of the first woven component portion, and
the plurality of first intersecting points are arranged side by side in the circumferential direction of the first woven component portion and arranged in the plurality of intersecting regions, respectively.

3. The synthetic resin stent according to claim 1, wherein
in a configuration in which the first intersecting points are arranged in the intersecting regions, respectively,
the third fibers are arranged in a state of being hooked by one or more of the first fibers, the second fibers and the fourth fibers, in relation to movement in a direction in which an overlapping portion of the third fibers and the fourth fibers shrinks in size, and
the fourth fibers are arranged in a state of being hooked by one or more of the first fibers, the second fibers and the third fibers, in relation to movement in a direction in which the overlapping portion of the third fibers and the fourth fibers shrinks in size.

4. The synthetic resin stent according to claim 3, further comprising
a plurality of configurations in which the first intersecting point is arranged in the intersecting region, wherein
the synthetic resin stent is configured to partly include a configuration, in which the third fibers and the fourth fibers are arranged in a state of being mutually hookable, in relation to movement in a direction in which the overlapping portion of the third fibers and the fourth fibers shrinks in size, and arranged in a state of not being hookable by the first fibers and the second fibers when the third fibers and the fourth fibers move.

5. The synthetic resin stent according to claim 1, wherein the second woven component portion is formed of synthetic resin fiber having an expansion force higher than the first woven component portion.

* * * * *